United States Patent
Imran et al.

(10) Patent No.: US 8,986,279 B2
(45) Date of Patent: Mar. 24, 2015

(54) METHODS AND ARCHITECTURE FOR POWER OPTIMIZATION OF IONTOPHORETIC TRANSDERMAL DRUG DELIVERY

(75) Inventors: Mir Imran, Los Altos Hills, CA (US); Dean P. Andersen, San Jose, CA (US); Vikram Malhotra, Riverside, CA (US); George Andrew Mangogna, Sunnyvale, CA (US)

(73) Assignee: InCube Labs, LLC, San Jose, CA (US)

(*) Notice: Subject to any disclaimer, the term of this patent is extended or adjusted under 35 U.S.C. 154(b) by 49 days.

(21) Appl. No.: 13/024,295

(22) Filed: Feb. 9, 2011

(65) Prior Publication Data

US 2011/0196283 A1 Aug. 11, 2011

Related U.S. Application Data

(60) Provisional application No. 61/303,284, filed on Feb. 10, 2010.

(51) Int. Cl.
*A61M 31/00* (2006.01)
*A61N 1/32* (2006.01)
*A61N 1/04* (2006.01)

(52) U.S. Cl.
CPC ............ *A61N 1/325* (2013.01); *A61N 1/044* (2013.01); *A61N 1/0448* (2013.01)
USPC ...................................................... 604/501

(58) Field of Classification Search
USPC ............................................ 604/20, 21, 501
See application file for complete search history.

(56) References Cited

U.S. PATENT DOCUMENTS

| | | | |
|---|---|---|---|
| 5,019,034 A * | 5/1991 | Weaver et al. | 604/20 |
| 5,042,975 A | 8/1991 | Chien et al. | |
| 5,246,418 A | 9/1993 | Haynes et al. | |
| 6,018,679 A * | 1/2000 | Dinh et al. | 604/20 |
| 6,047,208 A * | 4/2000 | Flower | 604/20 |
| 6,402,732 B1 * | 6/2002 | Flower et al. | 604/501 |
| 2004/0186417 A1 * | 9/2004 | Phipps et al. | 604/20 |

(Continued)

FOREIGN PATENT DOCUMENTS

WO WO 2007/050487 A2 5/2007

OTHER PUBLICATIONS

International Search Report, Written Opinion and Notice of Transmittal of same mailed Oct. 28, 2011 in International Application PCT/US2011/024259.

(Continued)

*Primary Examiner* — Kami A Bosworth
(74) *Attorney, Agent, or Firm* — Mahamedi Paradice LLP

(57) ABSTRACT

Embodiments of the invention provide an architecture, system and methods for optimizing power utilization for transdermal iontophoretic drug delivery which maintain a iontophoretic driving voltage at a reduced or even minimum value to support an iontophoretic delivery current. The reduced voltage reduces the power requirements for a transdermal iontohoretic delivery system during a period of drug delivery. Embodiments of an architecture for implementing this approach can utilize a controller which compares the desired current to the actual current and adjusts the voltage to reduce the amount of power used for iontophoretic drug delivery. The controller can comprise a state machine or microprocessor. Embodiments of the invention are particularly useful for extending the battery life of transdermal iontophoretic drug delivery systems.

32 Claims, 7 Drawing Sheets

(56) References Cited

U.S. PATENT DOCUMENTS

| | | | |
|---|---|---|---|
| 2006/0167403 A1* | 7/2006 | Henley et al. | 604/20 |
| 2008/0058703 A1* | 3/2008 | Subramony et al. | 604/20 |
| 2008/0287497 A1 | 11/2008 | Anderson et al. | |
| 2009/0204056 A1* | 8/2009 | Nitzan | 604/20 |
| 2010/0130910 A1* | 5/2010 | Berenson | 604/20 |

OTHER PUBLICATIONS

International Preliminary Report on Patentability as issued in corresponding application PCT/US2011/024259, dated Aug. 23, 2012.

* cited by examiner

METHODS AND ARCHITECTURE FOR POWER OPTIMIZATION OF IONTOPHORETIC TRANSDERMAL DRUG DELIVERY

RELATED APPLICATIONS

This application claims the benefit of priority of U.S. Provisional Patent Application Ser. No. 61/303,284, entitled "Methods and Architecture for Power Optimization of Iontophoretic Transdermal Drug Delivery", filed Feb. 10, 2010; which is fully incorporated by reference herein for all purposes.

FIELD OF THE INVENTION

Embodiments described herein relate to methods for power optimization for transdermal drug delivery systems. More specifically, embodiments described herein relate to methods for power optimization of iontophoretic transdermal drug delivery systems.

BACKGROUND

The typical form of treatment for a number of medical conditions such as diabetes, iron deficiency anemia and cancer includes oral and intravenous drug delivery. However, both oral and intravenous forms of drug delivery treatment for these and other conditions have a number of limitations. In many cases, oral delivery can have poor absorption particularly in the presence of other medications as well as a number of side effects. Intravenous limitations include the requirement to mix and store the medication in liquid form as well as the use of sterile techniques in administration. These can be particularly problematic in third world countries where adequate refrigeration and sterile needles are not readily available, limiting shelf life and exposing the patient to infection. Also, IV administration can include several risk factors including anaphylaxis and cardiovascular complications. Thus, there is a need for improved methods of drug delivery for many forms of treatment.

Transdermal iontophoresis is a non-invasive method of propelling high concentrations of drug or other therapeutic agents through the skin by repulsive electromotive force using a small electrical charge. In order to facilitate ease of use to the patient, iontophoretic transdermal devices are portable and thus include a portable power source such as a battery so that the device can be worn or carried by the patient. Further, in some instances it is desirable for such power sources to be able to provide power for a period of hours each day possibly over multiple days in order to allow the patient to receive a selected drug during this period. Thus battery life can be a factor in the usability of a transdermal iontophoretic delivery device for the patient so that patient need not change batteries over the course of a single treatment or even over many treatments. Thus there is a need for approaches for improving battery life for transdermal iontophoretic delivery devices and systems.

BRIEF SUMMARY

Embodiments of the invention provide an architecture, system and method for optimizing power used for the transdermal iontophoretic delivery of drugs and other therapeutic agents. Many embodiments provide an architecture, system and method for optimizing power used for the transdermal iontophoretic delivery of drugs and other therapeutic agents wherein the voltage used for driving transdermal iontophoresis (the driving voltage) is adjusted responsive to electrical parameters in the architecture and/or electrical circuit used for transdermal iontophoretic drug delivery. Such parameters can include the actual iontophoretic current, the total or lumped (herein total) resistance/impedance of the iontophoretic transdermal delivery circuit or the tissue resistance/impedance at the iontophoretic delivery site. As used herein, resistance refers to embodiments using a direct current for the iontophoretic delivery current and impedance refers to embodiments using an alternating current for the iontophoretic delivery current. In particular embodiments using an AC iontophoretic delivery current, the driving voltage is adjusted responsive to the total impedance between two electrodes used for iontophoretic current delivery.

In various aspects, the invention provides an approach for optimizing power utilization for transdermal iontophoretic drug delivery which maintains the iontophoretic driving voltage at the minimum value it takes to support a desired iontophoretic delivery current. Since the tissue impedance can change over time (e.g., due to tissue heating and changes the ion concentration in tissue), it is desirable to also change the iontophoretic voltage. Embodiments of this approach can utilize a controller which compares the desired delivery current to the actual delivered current and adjusts the driving voltage such that power used for iontophoretic delivery is reduced and even minimized. This in turn, extends both battery life and the delivery period for iontophoretic drug delivery. Thus, over the course of a drug delivery regimen of days, or even up to one to two weeks, a user need not remove a wearable iontophoretic delivery system to change a battery. This improves compliance with a particular drug delivery regimen and in turn, helps to maintain the desired concentration of drug in the patient's body over the course of a delivery period. This serves to improve clinical outcomes while reducing the incidence of over and/or under delivery of drug. Embodiments of the invention are particularly useful for improving compliance with drug delivery regimens over long periods of time such as those used for iron deficiency anemia, chemotherapy, pain management, diabetes, hypertension, blood volume management and other related conditions and diseases.

In one aspect, the invention provides a method for optimizing power for iontophoretic transdermal delivery of a therapeutic agent to a patient comprising applying a patch to a skin, with the patch comprising a therapeutic agent and at least one electrode. Typically, at least two electrodes will be applied, though three, four or even greater numbers may applied. The electrodes are then coupled to a power source comprising electrical circuitry and one or more portable batteries or other electrical storage means. Collectively, the patch and power source comprise an iontophoretic delivery system and the power source, patch and patient's skin comprise an iontophoretic delivery circuit for iontophoretic delivery. A selected current is then delivered to the skin from the power source through the patch/electrode to transport the therapeutic agent into the skin (using an electromotive force). An electrical parameter of the iontophoretic delivery circuit is then measured. Typically, this will include either the actual current delivered to tissue (herein delivery current) or the total resistance/impedance of the iontophoretic delivery circuit, though other resistance/impedance values are also considered. The voltage used to supply the delivery current to skin is adjusted responsive to the measured electrical parameter, wherein the voltage is adjusted to maintain the selected delivery current while minimizing power delivered from the power source. In many embodiments, the delivery current is an alternating current which can have a frequency in the range of 0.5 to 100 hz. Typically, the power source is an electrochemical battery such as a lithium or lithium ion or alkaline battery. The life of the battery can be extended as a result of the minimized delivered power. The minimized power can also be used to maintain the voltage and/or current of the battery above a minimum level during a period of transdermal therapeutic agent delivery. The delivery period can extend from several days, to a week or two or longer. In use, this approach allows the patient to wear and/or use a transdermal iontophoretic delivery device for a period of days or weeks or longer without having to take off the device to replace the batteries. This in turn, improves patient compliance with a medicinal regimen and helps maintain in vivo concentrations of the selected therapeutic agent at therapeutically effective levels improving clinical outcomes.

Another aspect the invention provides circuit architectures (herein architectures) for optimizing power for the iontophoretic transdermal delivery of a therapeutic agent. In one embodiment the architecture comprises a first and second electrode, a power source operably coupled with the first and second electrodes, a current source operably coupled to at least one of the first and second electrodes, a measurement device operably coupled to the current source and a controller operably coupled to the measurement device and the power source. At least one of the electrodes is positioned in or on or otherwise operably coupled to an iontphoretic transdermal patch for delivering the therapeutic agent to the patient. The power source can comprise a voltage source such as an electrochemical storage battery (e.g., lithium alkaline, etc.) and a voltage converter operably coupled to the voltage source. In such embodiments, the controller can be operably coupled to the voltage regulator. The controller can comprise one or more of a microprocessor or other digital controller, or a state device or other analog controller. The controller can also include logic for utilizing an input from the measurement device to generate an output sent to the voltage regulator so as to maintain current from the current source above a threshold level while minimizing power drawn from the power source including the battery. For digital embodiments of the controller the logic can be incorporated into one or more software modules which are operable on the controller and may be resident within the controller or stored in a memory device coupled to the controller. The measurement device can be configured as an impedance (resistance) measurement device, a current measurement device or other related electrical property measurement device known in the art, and may utilize Ohms law for measuring one or more electrical properties. In various embodiments the measurement device may include a resistor and operational amplifier (herein op-amp) or other amplifier device/circuit. For digitally based embodiments of the controller, the measurement device may also include an analog to digital converter (herein an A/D converter) for converting output signals from the measurement device into digital form. In such embodiments all components of the measurement device can be fabricated on a single integrated circuit. Also, all or portions of the entire architecture can be fabricated on a single integrated circuit such as an ASIC or other related circuit.

Further details of these and other embodiments and aspects of the invention are described more fully below, with reference to the attached drawing figures.

DETAILED DESCRIPTION OF THE INVENTION

Figure 1:
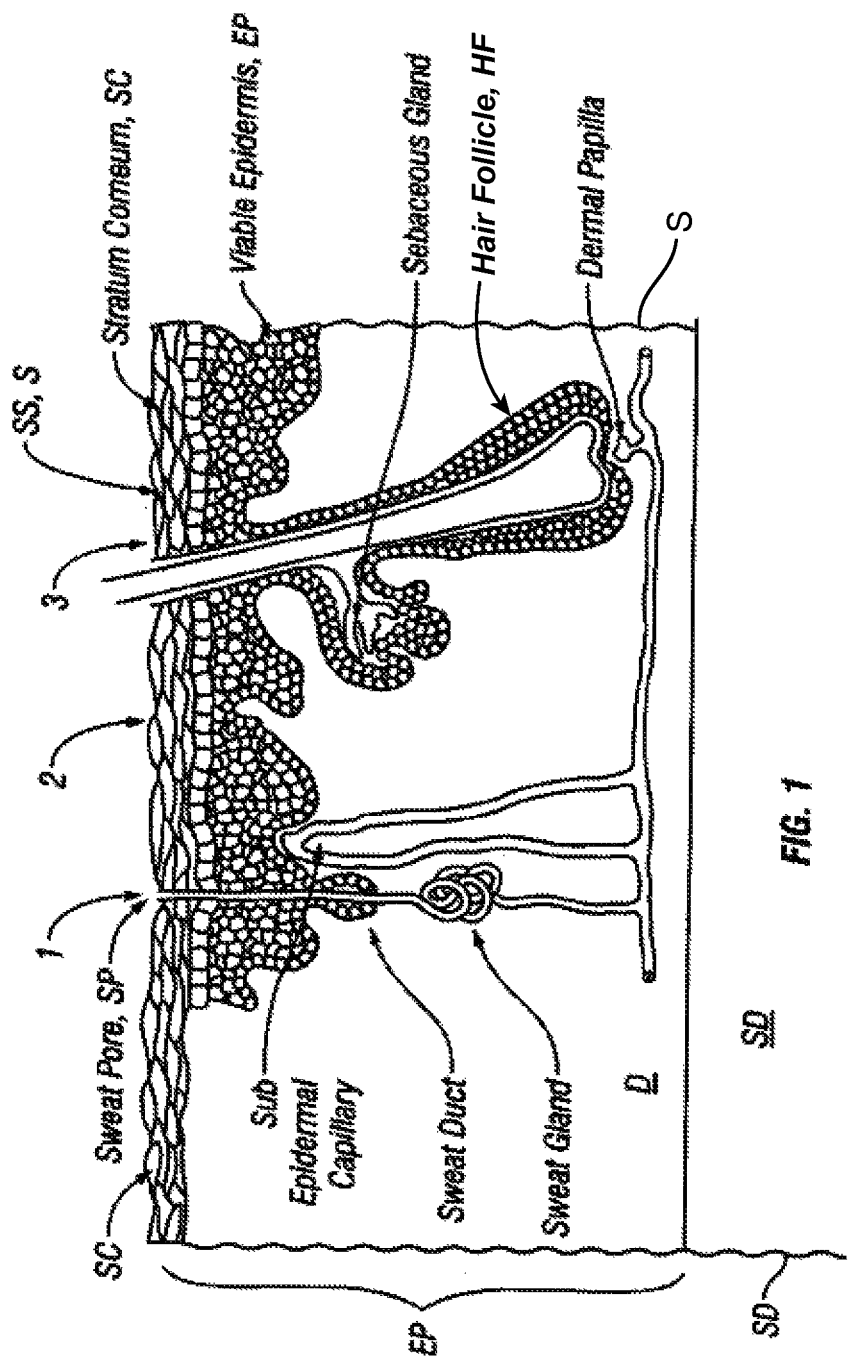
FIG. 1 is a cross sectional view showing the three main layers of the skin, the epidermis, the dermis and subcutaneous tissue as well as the passageways into the skin.
Figure 2:
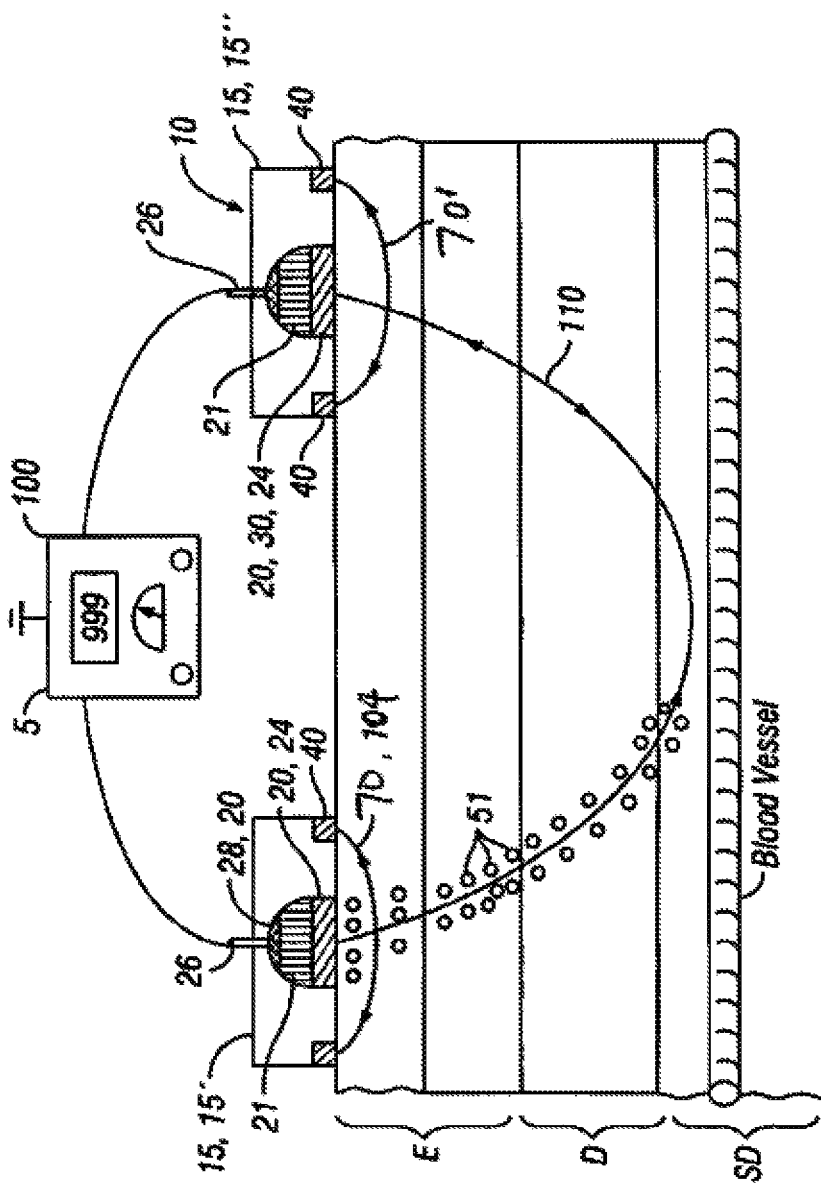
FIG. 2 is a lateral view of an embodiment of a system for the transdermal iontophoretic delivery of various therapeutic agents using delivery and lateral electrodes.

Many embodiments described herein provide a device, system and method for the transdermal iontophoretic delivery of various therapeutic agents. As used herein, the term transdermal delivery refers to the delivery of a compound, such as a drug or other therapeutic agent, through one or more layers of the skin (e.g., epidermis, dermis, etc). Referring now to FIG. 1, the layers of the skin include the epidermis EP, dermis D and subdermis SD. The upper most layer of the epidermis includes the stratum corneum SC, a dead layer of skin (having a thickness of about 10 to 40 μm) and the viable epidermis EP. Transdermal delivery can proceed by one of the three passage ways into the skin, via 1, the sweat pores SP, 2, the hair follicles HF or via permeation 3 through the epidermis EP (starting at the stratum corneum) and the dermis.

Iontophoresis is a non-invasive method of propelling high concentrations of a charged substance, known as the active agent, transdermally by repulsive electromotive force using a small electrical charge. The active agent can include a drug or other therapeutic agent. The charge is applied by an electrical power source to an active electrode assembly placed on the skin which contains a similarly charged active agent and a solvent in which it is dissolved. Current flows from the electrode assembly through the skin and then returns by means of a return or counter electrode assembly also placed on the skin. A positively charged electrode assembly, termed the anode will repel a positively charged active agent, or anion, into the skin, while a negatively charged electrode assembly, termed the cathode, will repel a negatively charged active agent, known as a cation into the skin.

Referring now to FIGS. 2-5, an embodiment of a system 5 for the transdermal iontophoretic delivery of a therapeutic agent 51 to a tissue site TS (such as the arm A) also referred to as a delivery site, on the skin S of patient, comprises at least two electrode assemblies 14 (FIG. 5) including an active electrode assembly 20 and a return electrode assembly 30; and a power supply 100. Active electrode assembly 20 is used to deliver the therapeutic agent through skin S via current delivered to the skin from power supply 100. Return electrode assembly 30 provides a return path for current to power supply 100. Collectively, the active and return electrode assemblies 20 and 30 comprise a transdermal iontophoretic delivery device 10 also described herein as patch device 10. In embodiments using an alternating current, both electrode assemblies 14 can be configured as active and return electrode assemblies 20 and 30 depending on the direction of current flow. In some cases for sake of brevity, electrode assembly 14, active electrode assembly 20 and/or return electrode assembly 30 will sometimes be referred to as electrode 14, active electrode 20 and return electrode 30.

In many embodiments, the electrode assemblies 14 (e.g., active and return assemblies 20 and 30) comprise or are otherwise disposed on one or more patches 15 configured to be applied to the skin surface. Patches 15 are conformable to a contour CR of a skin surface S and can be fabricated from layers of elastomeric or other flexible polymer material. In some embodiments, two or more electrode assemblies 14 including active and return electrode assemblies 20 and 30 can be placed on a single patch 15. In other embodiments, system 5 can include separate patches 15 for electrode assemblies 14, for example, a first patch 15' for the active electrode assembly 20 and a second patch 15" for the return electrode assembly 30. In other embodiments, three or more patches 15 can be used so as to have either multiple active electrode assemblies 20 or return electrode assemblies 30 or both. For example, in one embodiment system 5 can comprise three patches 15; including two patches containing active electrode assemblies 20 and a third patch 15 containing a return electrode assembly 30. Other combinations of multiple patches and electrode assemblies are also contemplated, e.g., four patches, two for active electrode assemblies 20 and two for return electrode assemblies 30.

Figure 4A:
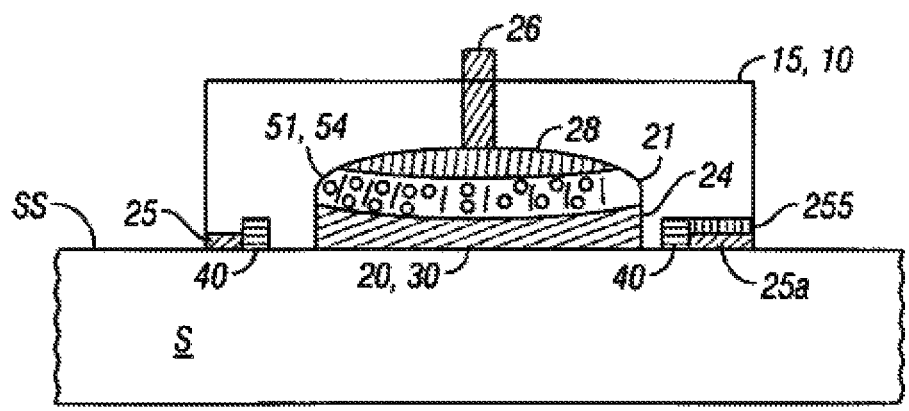
FIGS. 4a and 4b are side and top views showing an embodiment of a skin patch including an active electrode and lateral electrodes.
Figure 4B:
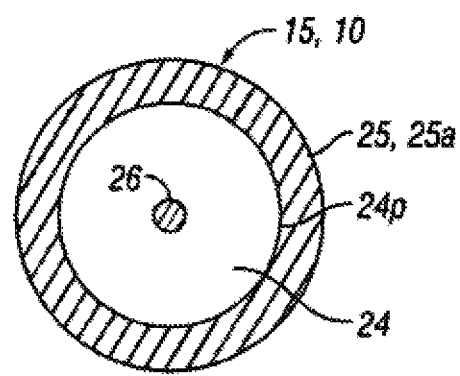

In many embodiments, active electrode assembly 20 can comprise a reservoir 21 for the therapeutic agent, a tissue contacting porous portion 24 in fluidic communication with the reservoir, an adhesive portion 25 for adhering the assembly to the skin, and an electrical connector 26 for coupling the electrode assembly 20 to an electrical power supply 100 as is shown in the embodiment of FIG. 4a. Reservoir 21 can be sized for the particular dose of therapeutic agent to be delivered. In various embodiments, the power supply 100 can include various features to facilitate use by medical personnel both in a hospital setting and in the field. For example, the power supply can include or be configured to be coupled to a bar code reader (not shown) for reading bar codes positioned on one or more of electrode assemblies 14, patches 15 or power supply 100.

Tissue contacting portion 24 is also conductive by virtue of being fabricated from conductive porous materials (e.g., conductive fibers) or becomes conductive by becoming wetted with conductive solution 54 (the conductivity being due to agent 51 or various electrolytes added to the solution) and thus functions as an electrode 20. Connector 26 can extend into or otherwise make electrical contact with tissue contacting portion 24. In some embodiments, connector 26 can be coupled to a conductive element 28 positioned within the electrode assembly 20 and coupled to conductive porous portion 24. One or more of conductive element 28, conductive layer 34 (described below) as well as lateral electrodes 40 (also described below) can comprise various conductive materials including stainless steel, carbon, AgCl or other conductive materials known in the art.

Figure 3A:
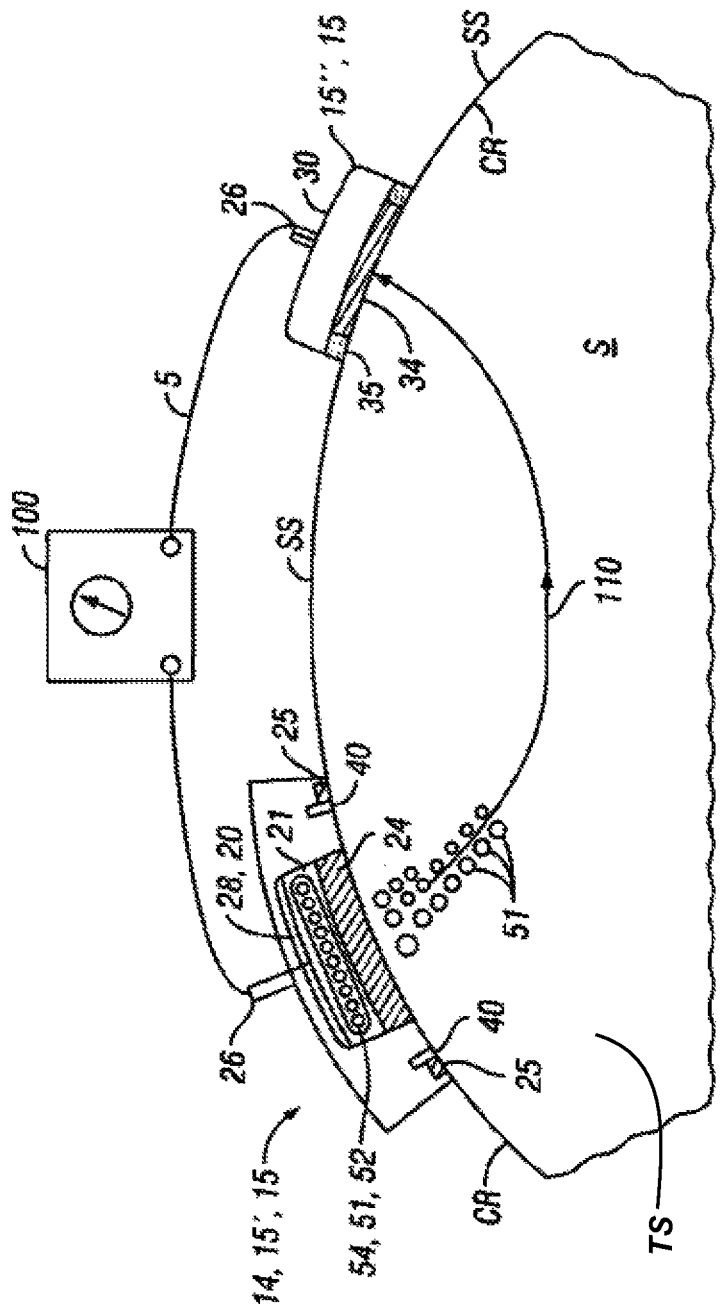
FIG. 3a is a schematic side view showing placement of an embodiment of a transdermal iontophoretic patch device on the surface of the skin, wherein the device comprises an active electrode assembly and a return electrode assembly.
Figure 3B:
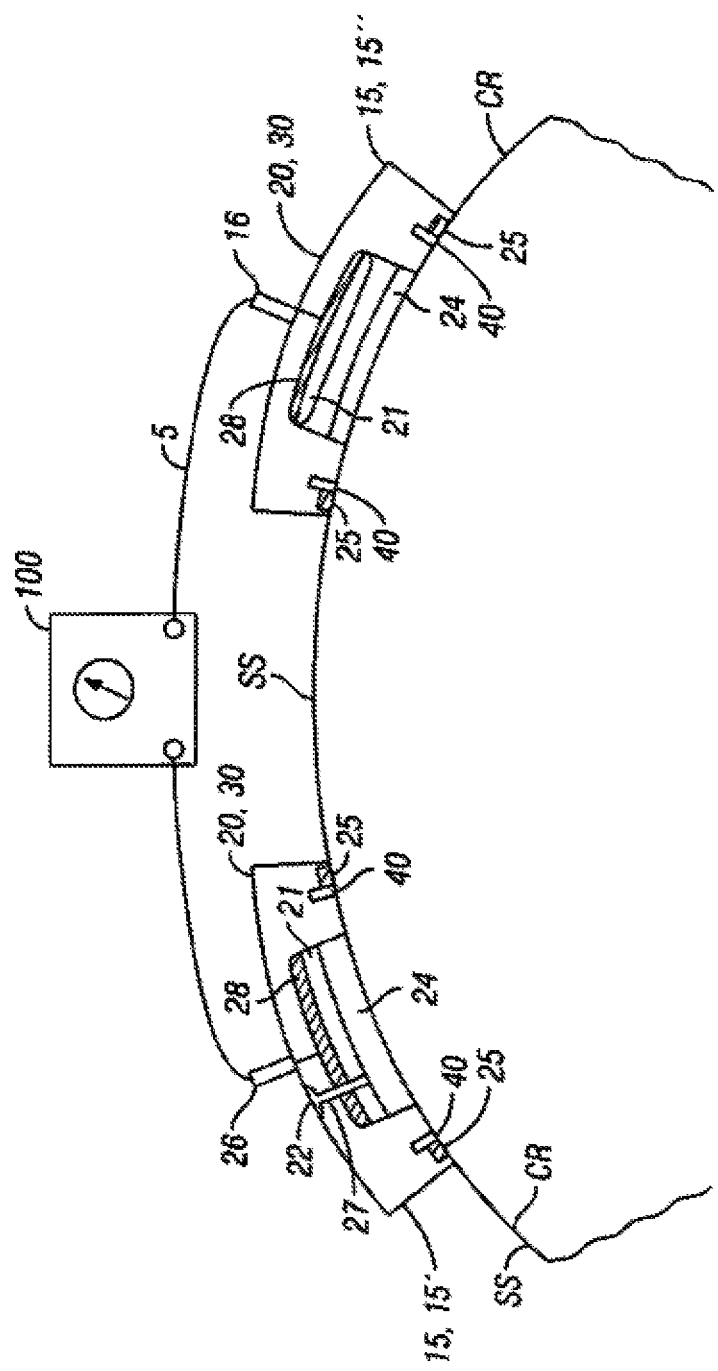
FIG. 3b is a schematic side view showing placement of an embodiment of transdermal iontophoretic patch device on the surface of the skin, wherein the device comprises two active electrode assemblies.

Typically, the therapeutic agent 51 will be dissolved in a therapeutic agent solution 54, also described as therapeutic agent composition 54 which is used to fill reservoir 21. In addition to agent 51, solution 54 can include one or more pharmaceutical excipients 52 such as preservatives. The viscosity of the solution 54 can be adjusted to have the solution readily wick from reservoir 21 into porous layer 24. Solution 54 can be preloaded into the reservoir 21 at the factory or can be added by medical personnel prior to use through means of a port 22, such as self sealing port allowing injection which is coupled to reservoir 21 via means of a channel 27 as is shown in the embodiment of FIG. 3b. Suitable therapeutic agents 51 can include without limitation ferric pyrophosphate or other iron containing compound for the treatment of iron deficient anemia, insulin or various glucagon like peptides for treatment of diabetes or other blood sugar regulation disorder, Fentanyl or other opioid compound for pain management and various chemotherapeutic agents for the treatment of cancer such as Paclitaxel.

The return electrode assembly 30 comprises a tissue contacting conductive layer 34, an adhesive layer 35 and a connector 26 for coupling the electrode assembly to the electrical power source. In many embodiments, the return electrode assembly 30 can have substantially the same elemental configuration as active electrode assembly 20 (e.g., a reservoir 21, conductive tissue contacting layer 24) so as to function as an active electrode assembly as is shown in the embodiment of FIG. 3b.

In many embodiments, patch 15 also includes one or more pair of electrodes known as lateral electrodes 40. Lateral electrodes 40 can be placed on either side of porous portion 24 at a selectable distance from the perimeter 24p of porous portion 24 as is shown in the embodiments of FIGS. 3a-3b and 4a-4b. Electrodes 40 can comprise various conductive materials including metals, graphite, silver chloride and other like materials. In various embodiments, all or a portion of electrode 40 can include an insulative coating so as to be a capacitively coupled electrode that delivers current to the skin via capacitive coupling. Electrodes 40 can be electrically isolated from electrodes 20 and 30 will typically include their own wave form generator circuits.

The lateral electrodes 40 are arranged with respect to porous portion 24 such that they result in a conductive pathway 104 which goes through the skin S underlying portion 24 and is substantially parallel to the skin. Embodiments of patch 15 that employ lateral electrodes 40 with delivery electrodes 20, allow for the flow of two currents, a first current 60 and a second current 70. First current 60 flows between electrodes 20 and 30 and serves to provide an electromotive force which acts to drive the therapeutic agent 51 into and across the layers of the skin S. The second current 70, known as sieving current 70, provides an electromotive force that acts on the therapeutic agent 51 in a direction parallel to the skin S so as to cause oscillation of therapeutic agent 51 in a direction parallel to skin S. This oscillation acts to sieve the therapeutic agent through pathways of lesser or least diffusional resistance in the skin. For embodiments where second patch 15" contains lateral electrodes 40 and is used to deliver therapeutic agent, a third current 70' can be delivered from lateral electrodes on the second patch 15" to also create a electromotive driving force 80 to oscillate the therapeutic agent substantially parallel to the skin surface underneath the second patch 15". Further description on the arrangement and use of lateral electrodes 40 including use in generating a sieving current is found in U.S. Provisional Patent Application Serial No's. 61/152,251 and 61/221,010 which are incorporated by reference herein in their entirety.

Figure 5:
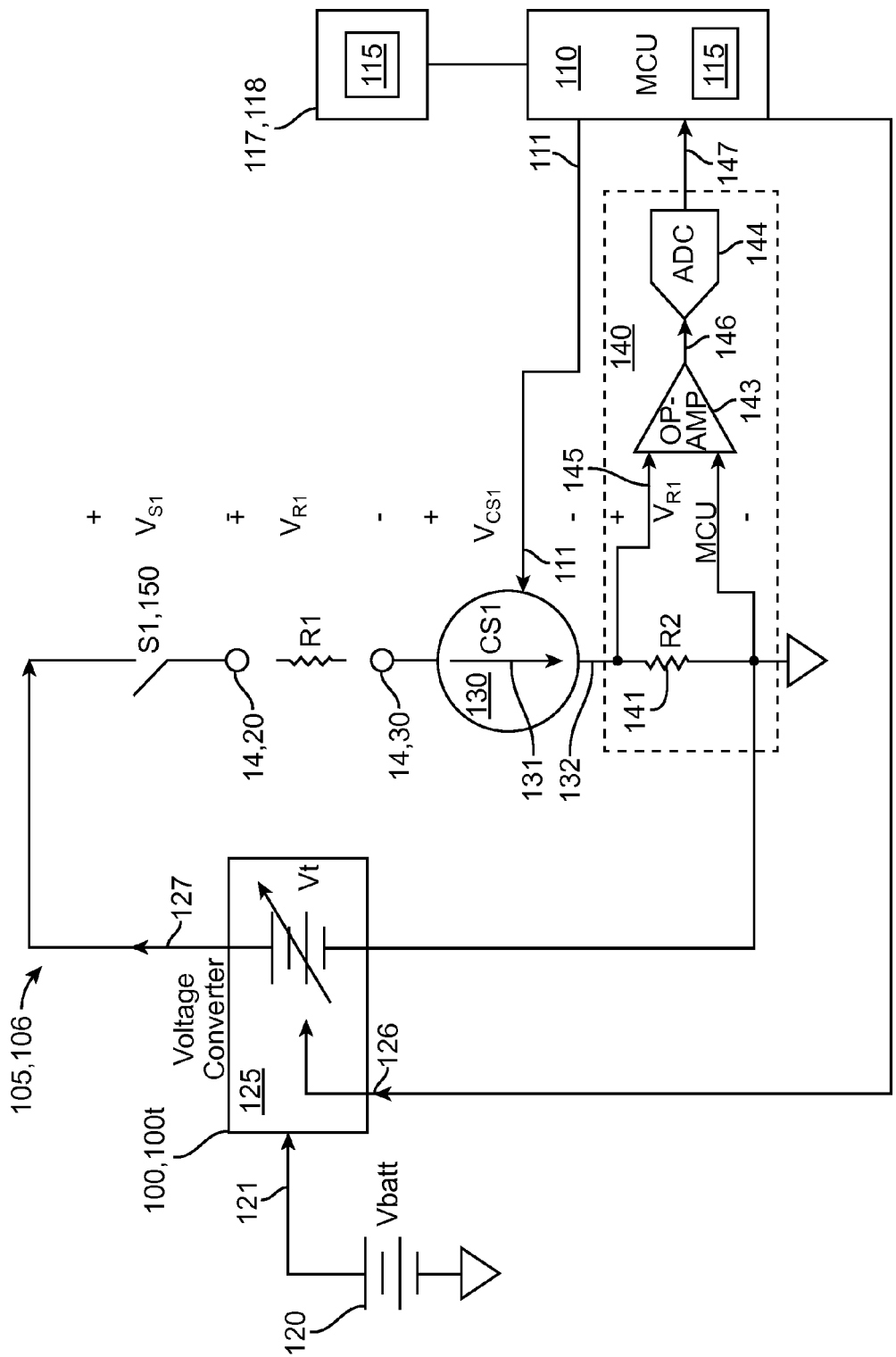
FIG. 5 is a schematic view showing an embodiment of a power optimizing architecture for use with iontophoretic transdermal drug delivery systems.
Figure 6:
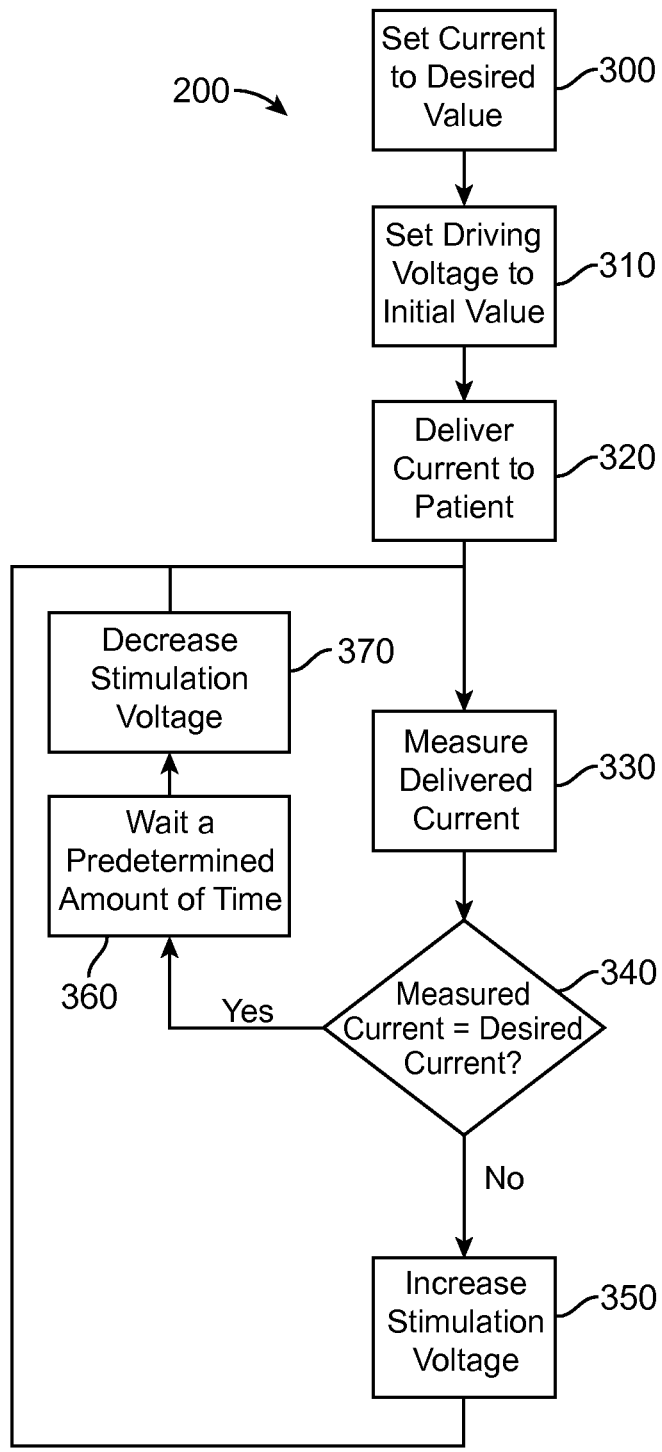
FIG. 6 is a flowchart of an algorithm of power optimization for use with iontophoretic transdermal drug delivery systems.

Referring now to FIGS. 5-6, embodiments of a power control architecture 105 for optimizing power supplied to a transdermal iontophoretic delivery system 5 will now be described. Architecture 105 can be configured to optimize power used by system 5 for iontophoretic drug delivery to a patient at a delivery site such as the skin or other site on or within the body (e.g., the eye, the tympanic membrane, buccal mucosa, intestinal mucosa, etc.). This, in turn, reduces power consumption and extends battery life of system 5 or other transdermal iontophoretic delivery system. Accordingly, embodiments of the architecture are particularly useful for extending the battery life for transdermal iontophoretic delivery systems.

Architecture 105 will typically comprise a power supply 100, at least two electrodes 14 (e.g., an active and return electrode), a controller 110, a current source 130, a current/impedance measurement device 140 and at least one switch 150. Many variations to this configuration are also contemplated, including for example, the inclusion of additional electrodes, sensors, filters (e.g., high pass, low pass, band pass, etc.), communication devices (e.g., an RF ID chip), various power management devices and other electronic devices and circuitry. All or portions of architecture 105 can be fabricated or otherwise positioned on a single integrated circuit (e.g., an ASIC or application specific integrated circuit) or on multiple integrated circuits (e.g., a chip set) that are operably coupled. All or portions of architecture 105 can comprise an iontophoretic delivery circuit 106 for iontophoretic drug delivery. Typically, circuit 106 comprises power source 100, patch/electrode(s) 14 and the patient's skin/tissue at delivery site TS.

Power supply 100 will typically include at least one voltage source 120 such as a portable battery or other electrical storage means coupled to a voltage converter 125. Suitable portable batteries include lithium, lithium ion, alkaline, or zinc-air battery with other chemistries also contemplated. As an alternative, voltage source 120 may, in various embodiments, comprise a capacitor (or other electrical storage means) or an energy harvesting device (e.g., a piezoelectric device) alone or in combination with another electrical storage means (e.g., a battery, capacitor, etc.). Voltage converter 125 serves to convert a voltage 121 from voltage source 120 to a desired voltage output voltage 127 used by architecture 105 and/or other circuitry and electrical components of system 5. Converter 125 can be fixed (e.g., step down, or step up) or variable and may be controllable by analog or digital inputs, e.g., from controller 110 or a manual input. The converter 125 can comprise various solid state devices (e.g., an integrated circuit) known in the art.

In many embodiments, power supply 100 can comprise a variable power supply 100t which may be controlled by a controller 110 or other control means (e.g., a remote controller). In an exemplary embodiment, variable power supply 100t comprises a portable battery 120 and a variable voltage converter 125 that is controllable by inputs 126 from controller 110. Inputs 126 can comprise digital or analog inputs (or a combination thereof), depending upon choice of a digital or analog controller 110. In this and related embodiments, converter 125 can be used to convert battery voltage 121 in the range from about 1.5 to 9 volts to an output voltage 127 in the range of about 10 to 100 volts, with other ranges also contemplated.

Controller 110 is used to control one or more electrical parameters of system 10 including the iontophoretic driving voltage and delivery current. Typically, it will be operably coupled to one or more of power supply 100, voltage converter 125, current source 130 and measurement device 140. It may also be coupled to or even integral with one or more other electrical devices, circuitry, sensors, electrodes (e.g., electrodes 20 and 30), communication devices (e.g., an RF chip) and other related components. Controller 110 includes or is otherwise configured to implement logic for utilizing an input such as input 147 from measurement device 140, to generate an output signal such as single 126 to minimize power drawn from power supply 100 including battery 110 while maintaining the current used by circuit 106 above a threshold level. In this way, battery life can be extended during periods of iontophoretic transdermal drug delivery utilizing circuit 106. Such logic can be incorporated into one or more software modules 115 described herein.

In various embodiments, controller 110 can comprise a microprocessor, ASIC, state machine or other logic resource known in the art and is configured to perform one or more control functions for architecture 105. In preferred embodiments, controller 110 comprises a digitally based controller such as a microprocessor. In some embodiments, controller 110 may include one or more control modules 115 that comprise a software program, subroutine or other electronic instruction set digitally stored within controller 110 or memory device 117 or other memory resources 118 coupled to controller 110. Modules 115 can be configured to control one or more electrical parameters of architecture 105 and system 5 including various voltages, currents (e.g., an iontophoretic delivery current), duty cycles, total delivered current and like parameters. Modules 115 can be pre-stored in controller 110 or downloaded from a memory device 117 coupled to the controller 110 or from a separate computer or the internet or other distributed network. In various embodiments, a physician or other medical caregiver can download one more modules 115 (corresponding to one or more drug delivery regimens) wirelessly using the internet and a portable wireless communication device such as a cell phone or tablet based device such as the Apple® Ipad®.

Current source 130 is used to control the current 132, also known as iontophoretic delivery current 132 (herein delivery current) delivered to electrode assemblies 20. Current source 130 is typically a controllable current source and may be controlled by one or more inputs 132 (digital, analog or a combination) from controller 110 or other control means. Accordingly, current source 130 may comprise various controllable current sources known in the art including various digitally controlled programmable current sources. Switch 150 is used to control the direction of current flow from current source 130 and may correspond to an H-bridge and other devices known in the art for controlling the direction of current flow.

Current measurement device 140 is configured to measure the iontophoretic delivery current delivered to the patient. It typically comprises a resistor 141, (also described as R2) an op-amp device 143 and an analog to digital (AD) converter 144. As shown in the embodiment of FIG. 5, device 140 functions by measuring a voltage across a known resistor and then digitally converting that signal which is then fed into controller 110. Specifically, a voltage 145 across resistor R2, 141 is fed into op-amp device 143, with the output 146, digitally converted by A/D (Analog to Digital) converter 144 into a digital signal 147 that is inputted into controller 110. Controller can then convert signal 147 into a current by applying ohms law (I=V/R). Other configurations for measuring current 132 are also contemplated. In an alternative embodiment, measurement device 140 can be an impedance measurement device that has a similar configuration to current measurement device 140 so as to measure tissue impedance (e.g., the impedance between electrode assemblies 14) over a range of frequencies, such as for example from about 0.01 to 1000 hz, and digitally convert that output signal into a digital signal 147 that is fed into control 110.

According to one or more embodiments of methods of using architecture 105, prior to or during a period of iontophoretic drug delivery, controller 110 sends a signal 111 to set current source 130 to a desired output delivery current 131. The actual current 132, delivered from current source 130 is then measured by measurement device 140 by sensing the voltage across series resistor 141, R2 and then applying ohms law (I=V/R). Controller 110 then compares the actual and desired currents 132 and 131 and sends a signal 126 to voltage converter 125 to change the output voltage 127 to obtain the desired delivery current 131. In addition, or as a supplement to use of current 132, controller 110 may use other various electrical parameters of architecture 105, and delivery circuit 106 as an input to modify the iontophoretic delivery current. Such parameters can include without limitation, the total resistance/impedance of architecture 105 and the total resistance/impedance R1 between electrodes 14 and/or the tissue impedance at the delivery site TS. The latter value can be obtained by use of a sensor placed on or in the skin at the delivery site TS. In some embodiments, the sensor can comprise electrode 14, such as active electrode 20.

The control algorithm used by controller 110 for controlling current 132 may comprise one or more of a proportional (P), integral (I), derivative (D), PI, or PID based algorithm. Additionally, the control algorithm may be included in a software module 115 resident within controller 110 as is described herein.

R1 is a lumped resistance representing the impedance between the electrode assemblies 14 (e.g., active and return electrode assemblies 20 and 30). The lumped resistance R1 comprises the resistance/impedance of the skin and other tissue through which iontophoretic current from current source 130 passes. The total voltage (VST) required is the sum of all the voltage drops across the components of architecture 105. These voltages are depicted as VST, VR1, VCS, and VR2 as is shown in the embodiment of FIG. 5. Ideally though not necessarily, the voltage required by the load, VR1, is large compared to the other voltages (e.g., VCS, VR2, etc.).

In particular embodiments for optimal power efficiency, Vt may be set to approximately the sum, or slightly above the sum, of the values of VR1, VCS, and VR2. Table 1, illustrates the power savings for an iontophoretic delivery system 5/device 10 that is achieved through use of power optimization methods described herein for various currents and impedance loads. As shown in the table, power saving of 59% or more can be achieved.

TABLE 1

| Programmed Current (mA) | Load Impedance (Ohms) | Required Stimulation Voltage (V) | Vt without optimal energy method (V) | Vt with optimal energy method (V) | Power Savings |
|---|---|---|---|---|---|
| 2 | 20000 | 40 | 80 | 44 | 45% |
| 3 | 10000 | 30 | 80 | 33 | 59% |
| 3 | 25000 | 75 | 80 | 80 | 0 |

FIG. 6 illustrates an embodiment of a power optimization algorithm 200 for implementing methods for optimizing power used for the iontophoretic delivery of a therapeutic agent to a patient. These and related methods can be implemented using an embodiment of architecture 105 or related power optimization architecture. However, other architectures are also contemplated. It should be appreciated that the order of these steps in the algorithm is exemplary and that the steps need not be done in the sequence described. Also only a portion of the steps in the algorithm need be used and others can be added or substituted. For example, as described below, a current measurement step can be substituted with an impedance measurement step.

In a step 300, a target iontophoretic delivery current is set by communication from controller 110 to the current source 120. Then in a step 310 a driving voltage is set to an initial value by communication from controller 110 to voltage converter 135. Then in a step 320 current is delivered to the patient and in step 330 the delivered current is measured using current/voltage measurement device 140. As an alternative to current measurement, step 330 may comprise an impedance measurement step. The impedance that can be measured can include one or more of the total impedance of system 5, the total impedance between electrodes 14 and the tissue impedance at the drug delivery site. The measured and desired current (or impedance) are compared in a step 340. If the measured current or impedance is not at the desired level, the driving/stimulations voltage is increased in a step 350. If the current is at the desire level, then the algorithm waits a predetermined amount of time, in a wait step 360 before decreasing the driving/stimulation voltage in step 370. The wait period can be in the range from about 0.001 to 10 seconds or longer. After step 370, the algorithm then cycles back to current measurement step 330. This cycle can then be repeated throughout the entire period of iontophoretic current delivery in a substantially continuous fashion or for a selected portion thereof. Examples of measuring the electrical property for selected portions of time include variable or fixed intervals in the range of about 0.001 to 1.0 second, and/or where periods between intervals may span the range of about 0.001 to 1.0 second. Moreover, the electrical property may be measured before and during the period current is delivered to the skin. The amount that the stimulating voltage is decreased or increased in steps 350 and 370 can range from about 0.01 to about 10% of the stimulating voltage with lower and higher values contemplated. In specific embodiments, the amount of voltage increase or decrease can be 0.05, 0.1, 0.25, 0.5, 1, 5, or 7.5% of the stimulating voltage. The amount of voltage increase or decrease can itself vary depending upon one or more variables such as the initial stimulation voltage levels, impedance levels and/or a user input.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, the iontophoretic patch can be modified in size, shape and dose of therapeutic agent for different medical conditions, different tissue sites as well as for various pediatric applications. Additionally, the power optimization algorithm can also be modified for skin type, therapeutic agent dose, as well as various pediatric applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for optimizing power for iontophoretic transdermal delivery of a therapeutic agent to a patient in need thereof, the method comprising:
    applying a patch to the skin of the patient, the patch comprising a therapeutic agent and at least one electrode;
    coupling the at least one electrode to a power source;

delivering a current to the skin from the patch to transport the therapeutic agent into the skin;

measuring a delivered current in a circuit comprising the patient and the power source;

comparing the measured current to a desired current; and adjusting a voltage responsive to the comparison, wherein decreases in the voltage are made after a wait period to determine if the desired current is achieved; and wherein the voltage is adjusted to achieve and maintain the desired current while minimizing power delivered from the power source.

2. The method of claim 1, wherein power from the power source is reduced by up to about 45 percent by adjustment of the voltage.

3. The method of claim 1, wherein power from the power source is reduced by up to about 60 percent by adjustment of the voltage.

4. The method of claim 1, wherein the therapeutic agent comprises an iron containing compound for the treatment of iron deficiency anemia.

5. The method of claim 1, wherein the therapeutic agent comprises insulin or a glucagon-like peptide for the treatment of a blood sugar regulation disorder.

6. The method of claim 1, wherein the therapeutic agent comprises fentanyl or an opioid for pain management.

7. The method of claim 1, further comprising measuring an electrical property of a circuit comprising the patient and the power source.

8. The method of claim 7, wherein the electrical property is measured over a range of frequencies.

9. The method of claim 8, wherein the range of frequencies is from about 0.01 to about 1000 hz.

10. The method of claim 8, wherein the electrical property is measured using a sensor.

11. The method of claim 10, wherein the sensor is coupled to at least one of the power source or a controller coupled to the power source.

12. The method of claim 10, wherein the sensor is positioned on or in the patch.

13. The method of claim 10, wherein the sensor comprises the at least one electrode.

14. The method of claim 7, wherein the electrical property is measured in a substantially continuous fashion during a period when current is delivered to the skin.

15. The method of claim 7, wherein the electrical property is measured at fixed intervals during a period when current is delivered to the skin.

16. The method of claim 15, wherein an interval duration is in a range of about 0.001 to 1 second.

17. The method of claim 15, wherein a period between intervals is in a range of about 0.001 to 1 second.

18. The method of claim 1, wherein the power source is an electrochemical battery and battery life is extended by adjustment of the voltage.

19. The method of claim 18, wherein the battery is a lithium or alkaline battery.

20. The method of claim 18, wherein a battery voltage or current is maintained above a minimum level for a therapeutic agent delivery period as a result of the minimized delivered power.

21. The method of claim 20, wherein the delivery period is up to about one week.

22. The method of claim 20, wherein the delivery period is up to about two weeks.

23. The method of claim 18, wherein the current has a frequency in a range from about 0.5 to 100 Hz.

24. The method of claim 1, wherein the current is an alternating current.

25. The method of claim 1, wherein the voltage is adjusted using a controller.

26. The method of claim 25, wherein the controller is an analog device, a state machine, a digital controller or a microprocessor.

27. The method of claim 25, wherein the controller utilizes a software module to adjust the voltage.

28. A method for optimizing power for iontophoretic transdermal delivery of a therapeutic agent to a patient in need thereof, the method comprising:

applying a patch to the skin of the patient, the patch comprising a therapeutic agent and at least one electrode;

coupling the at least one electrode to a power source;

delivering a selected current to the skin from the patch to transport the therapeutic agent into the skin;

measuring an electrical impedance of the patient;

comparing the measured impedance to a desired impedance; and adjusting a voltage responsive to the comparison, wherein decreases in the voltage are made after a wait period to determine if the desired impedance is achieved and wherein the voltage is adjusted to maintain the selected current while minimizing power delivered from the power source.

29. The method of claim 28, wherein the impedance is measured in a volume of tissue between the at least one electrode and a return electrode applied to the skin of the patient.

30. The method of claim 28, wherein the impedance is measured in a circuit comprising at least two of the at the least one electrodes, the patient's tissue and the power source.

31. A method for optimizing power for iontophoretic transdermal delivery of a therapeutic agent to a patient in need thereof, the method comprising:

applying a patch to the skin of the patient, the patch comprising a therapeutic agent and at least one electrode;

coupling the at least one electrode to a power source;

delivering a current to the skin from the patch to transport the therapeutic agent into the skin;

measuring a delivered current and another electrical property in a circuit comprising the patient and the power source;

comparing the measured current to a desired current; and adjusting a voltage responsive to the comparison and the other electrical property, wherein decreases in the voltage are made after a wait period to determine if the desired current is achieved, and wherein the voltage is adjusted to achieve and maintain the desired current while minimizing power delivered from the power source.

32. The method of claim 31, wherein the other electrical property is one of a skin impedance, a skin resistance, a lumped impedance, a lumped resistance or a delivered current.

* * * * *